US00PP12070P2

(12) United States Plant Patent
van Gaalen

(10) Patent No.: US PP12,070 P2
(45) Date of Patent: Aug. 28, 2001

(54) PHLOX PLANT NAMED 'GOLDMINE'

(75) Inventor: Irenaeus Antonius Maria van Gaalen, Den Hoorn (NL)

(73) Assignee: Witteman + Co.'Multiflora' B.V., Hillegom (NL)

( * ) Notice: Subject to any disclaimer, the term of this patent is extended or adjusted under 35 U.S.C. 154(b) by 0 days.

(21) Appl. No.: 09/484,659

(22) Filed: Jan. 18, 2000

(51) Int. Cl.[7] ..... A01H 5/00
(52) U.S. Cl. ..... Plt./320
(58) Field of Search ..... Plt./320

(56) References Cited

PUBLICATIONS

UPOV–ROM GTITM Computer Database, Mar. 2000, GTI Jouve Retrieval Software, citation for 'Goldmine'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Phlox plant named 'Goldmine', characterized by its unique green and light yellow variegated foliage; upright plant habit; numerous bright purple flowers; and good garden performance.

2 Drawing Sheets

BACKGROUND OF THE INVENTION

The present Invention relates to a new and distinct cultivar of Phlox plant, botanically known as *Phlox paniculata*, and hereinafter referred to by the cultivar name Goldmine.

The new Phlox is a naturally-occuring whole plant mutation of the *Phlox paniculata* cultivar Kirchenfurst. The new Phlox was discovered by the Inventor in a controlled environment in Den Hoorn, The Netherlands, within a population of plants of 'Kirchenfurst' in 1998. The selection of this new Phlox was based on its unique variegated foliage. Plants of the cultivar Kirchenfurst have solid green-colored foliage.

Asexual reproduction of the new cultivar by vegetative cuttings taken at Den Hoorn, The Netherlands, has shown that the unique features of this new Phlox are stable and reproduced true to type in successive generations.

SUMMARY OF THE INVENTION

Plants of the cultivar Goldmine have not been observed under all possible environmental conditions. The phenotype may vary somewhat with variations in environment such as temperature, light intensity, daylength, and fertilizer rate without, however, any variance in genotype.

The following traits have been repeatedly observed and are determined to be the unique characteristics of 'Goldmine'. These characteristics in combination distinguish 'Goldmine' as a new and distinct cultivar:

1. Unique green and light yellow variegated foliage.
2. Upright plant habit.
3. Numerous bright purple flowers.
4. Good garden performance.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Phlox.

The photograph at the top of the first sheet comprises a side perspective view of typical flowering plants of 'Goldmine', grown in the landscape.

The photograph at the bottom of the first sheet comprises a close-up view of typical flowers of 'Goldmine'.

The photograph at the top of the second sheet comprises a close-up view of typical leaves (upper, mature leaf; lower, young leaf) and typical flowers of 'Goldmine'.

The photograph at the bottom of the second sheet comprises a close-up view of upper and lower surfaces of typical leaves (left, mature leaves; right, young leaves) of 'Goldmine'. Plants used for the description were about 30 weeks old.

DETAILED BOTANICAL DESCRIPTION

The following observations, measurements and values describe plants of the new cultivar grown under outdoor conditions during the summer in Den Hoorn, The Netherlands. Color references are made to The Royal Horticultural Society Colour Chart except where general terms of ordinary dictionary significance are used.

Botanical classification: *Phlox paniculata* cultivar Goldmine.

Parentage: Naturally-occurring whole plant mutation of *Phlox paniculata* cultivar Kirchenfurst, not patented.

Propagation:

*Type cutting.*—Vegetative cuttings.

*Time to produce a rooted liner.*—About 30 days during the spring in Den Hoorn, The Netherlands.

*Root description.*—Fine.

Plant description:

*Form.*—Upright, conical.

*Usage.*—Perennial garden plant.

*Crop time.*—From cuttings, about 30 weeks are required to produce fully-grown flowering plants in 1.5-liter containers.

*Plant height* (*from soil level to top of plant plane*).—About 90 cm.

*Area of spread.*—About 25 to 30 cm.

*Vigor.*—Moderate.

*Branching habit.*—Freely basal branching; clumping.

*Stems.*—Length: About 90 cm. Diameter: About 2 mm. Internode length: About 2.5 cm. Texture: Smooth. Color: Green, 143B to 143C with anthocyanin, 187A.

*Foliage description.*—Leaves simple, opposite, generally symmetrical, durable and long persisting. Length: About 9 cm. Width: About 3.5 cm. Shape: Elliptic. Apex: Acute. Base: Attenuate. Margin: Entire. Texture: Somewhat leathery; slightly ribbed; smooth, glabrous. Color: Variegated with irregular central green patterns surrounded by irregular light yellow patterns extending towards margins. Young foliage, upper surface: Center, 137A and 137B; margins, 12A, 12B and 12C. Young foliage, lower surface: Center, 191A; margins, 11A and 11B. Mature foliage, upper surface: Center, 137A, 137B and 138A; margins, 11D and 158A. Mature foliage, lower surface; Center, 191A; margins, 158A and 158B. Petiole: Length: About 2 mm. Diameter: About 2 mm. Color: 142B to 143D.

Flower description:

*Flower type and habit.*—Bright single purple flowers arranged in panicles; flowers face upward and outward. Flowers self-cleaning. Flowering continuous.

*Natural flowering season.*—Flowering occurs during the summer from July to early September in Den Hoorn, The Netherlands.

*Quantity.*—Very freely flowering with about 25 open flowers per stem and about 200 open flowers and flower buds on mature plants.

*Fragrance.*—Moderate to moderately strong; pleasant sweet fragrance typical of species.

*Flower longevity on the plant.*—About 6 days depending on weather conditions.

*Flower longevity as a cut flower.*—About 10 to 14 days.

*Flower buds, about two days before opening.*—Length: About 1.2 cm. Diameter: About 3 mm. Shape: Ovate. Color: 71A to 72A.

*Corolla.*—Arrangement: Five-parted, fused at base into a slender tube, salverform. Flower diameter: About 3.2 cm. Flower tube length: About 2.5 cm. Petal length from throat: About 1.4 cm. Petal width: About 1.7 cm. Petal shape: Beyond tube, flabellate. Petal apex: Rounded. Petal margin: Entire. Texture: Smooth, velvety; tube, sparsely covered with very short, less than 0.5 mm, grayish hairs. Petal color: When opening, upper surface: 71A; base, 60A. When opening, lower surface: 72B. Opened flower, upper surface: 71A; base, 60A. Opened flower, lower surface: 72B.

*Calyx.*—Calyx length: About 2.5 cm. Calyx width: About 3.2 cm; base of tube, about 3 mm. Sepal arrangement: Five fused at base, campanulate. Sepal shape: Linear. Sepal apex: Acuminate. Sepal margin: Entire. Sepal texture: Smooth. Sepal color, upper and lower surfaces: 183A, fading towards the base; 186D at margins.

*Peduncle.*—Angle: Upright to about 65° to stem. Strength: Moderate. Length: About 5 mm. Color: 187A.

*Reproductive organs.*—Stamens: Stamen number: Five, fused to petals in the corolla tube. Anther shape: Elliptic to ovate; basifixed. Anther length: About 1.5 mm. Anther color: Close to 11D. Pollen amount: Moderate. Pollen color: Close to 11D. Pistils: Pistils number: One. Stigma shape: Three-parted. Stigma color: 157A. Style length: About 1.9 cm. Style color: 187A. Ovary color: 141C.

*Seed.*—Seed production has not been observed.

Disease resistance: Resistance to pathogens common to Phlox has not been observed.

It is claimed:

1. A new and distinct cultivar of Phlox plant named 'Goldmine', as illustrated and described.

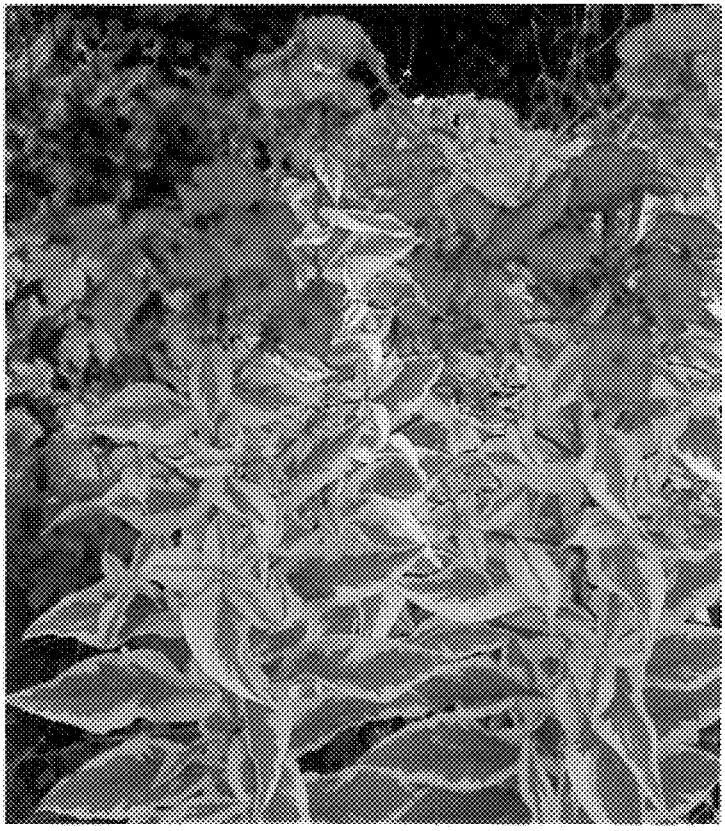
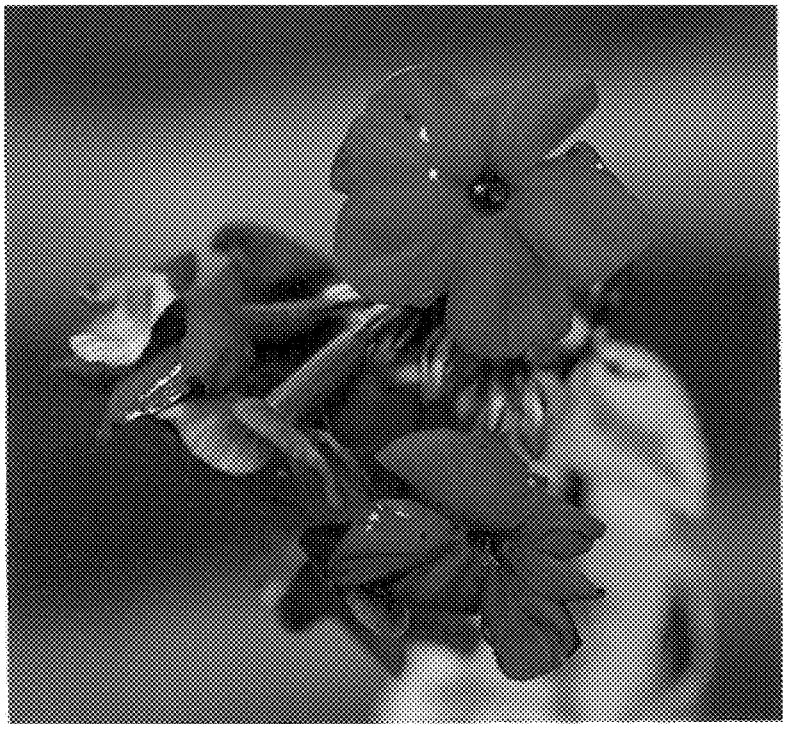

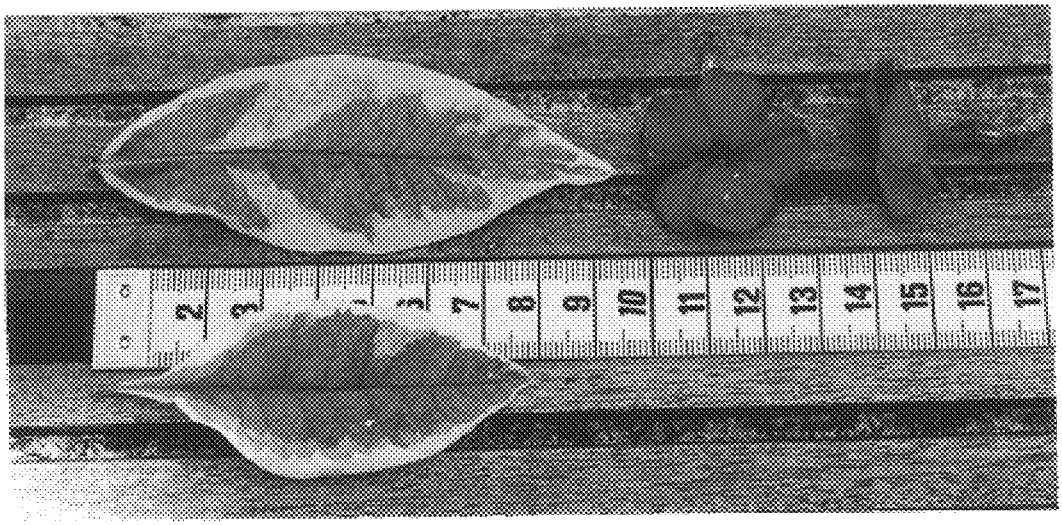
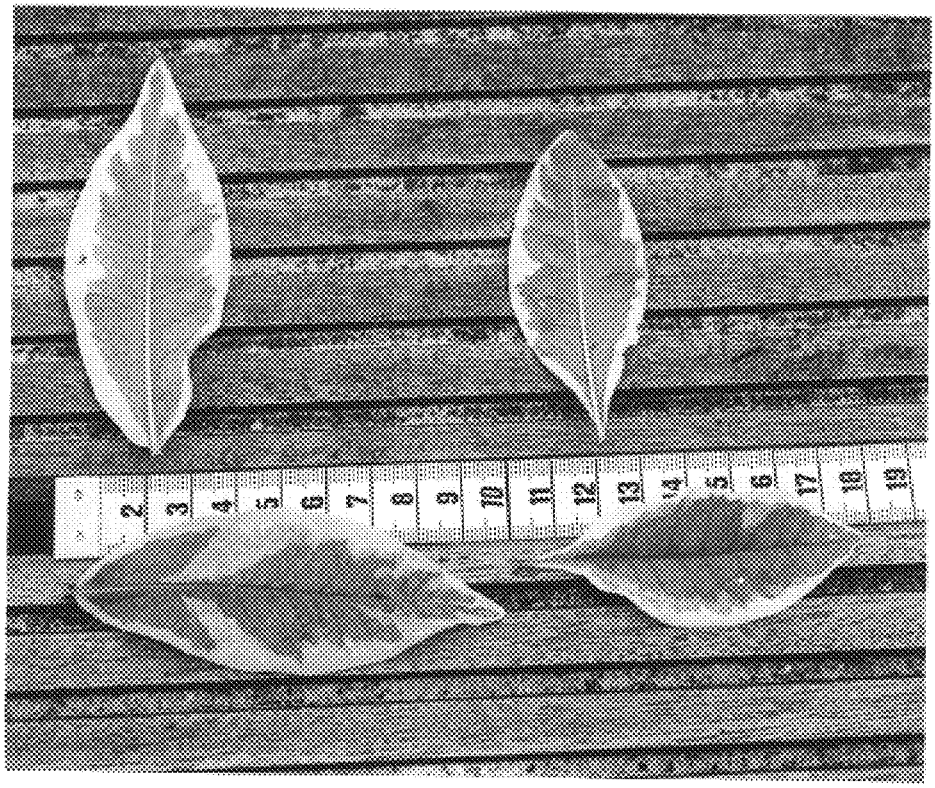

* * * * *